(12) United States Patent
Ferrera et al.

(10) Patent No.: US 6,585,688 B2
(45) Date of Patent: Jul. 1, 2003

(54) DILATATION CATHETER BALLOON MADE FROM PEN BASED HOMOPOLYMER OR RANDOM COPOLYMER

(75) Inventors: David A. Ferrera, Acton, MA (US); Ronald a. Sahatjian, Lexington, MA (US); Andrew J. Campbell, Reading, MA (US); George C. Michaels, Westford, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/045,554

(22) Filed: Jan. 14, 2002

(65) Prior Publication Data

US 2002/0122903 A1 Sep. 5, 2002

Related U.S. Application Data

(63) Continuation of application No. 08/927,662, filed on Sep. 10, 1997, now Pat. No. 6,358,227.

(51) Int. Cl.[7] ............................................. A61M 29/00
(52) U.S. Cl. .................. 604/96.01; 604/103.06
(58) Field of Search ................... 604/96–102, 103.06; 606/192, 194; 525/92 A

(56) References Cited

U.S. PATENT DOCUMENTS

| | | | |
|---|---|---|---|
| 4,154,244 A | 5/1979 | Becker | 128/349 |
| 4,820,349 A | 4/1989 | Saab | 128/344 |
| RE32,983 E | 7/1989 | Levy | 428/36.92 |
| 4,963,313 A | 10/1990 | Noddin et al. | 264/573 |
| RE33,561 E | 3/1991 | Levy | 428/36.92 |
| 5,189,140 A | 2/1993 | Nakane et al. | 528/272 |
| 5,195,969 A | 3/1993 | Wang et al. | 604/96 |
| 5,223,205 A | 6/1993 | Jackowski et al. | 264/521 |
| 5,264,260 A | 11/1993 | Saab | 428/35.5 |

(List continued on next page.)

FOREIGN PATENT DOCUMENTS

| | | | |
|---|---|---|---|
| EP | 0457456 | 11/1991 | A61M/25/00 |
| EP | 0745395 | 4/1996 | A61L/29/00 |
| EP | 0 747 070 | 12/1996 | |
| EP | 0 768 097 | 4/1997 | |
| WO | 92/19440 | 11/1992 | B29C/49/00 |
| WO | 95/22367 | 8/1995 | A61M/25/00 |
| WO | 96/00752 | 1/1996 | |
| WO | 96/04951 | 2/1996 | A61M/25/00 |

OTHER PUBLICATIONS

JP abstract of patent No. 2509016; publication No. 05–15603.
JP abstract of patent No. 2975803; publication No. 06/296693.

(List continued on next page.)

Primary Examiner—Sharon Kennedy
(74) Attorney, Agent, or Firm—Vidas, Arrett & Steinkraus

(57) ABSTRACT

A balloon for a medical device has a structural layer of a highly crystallized PEN polymer material. The PEN polymer material a polyethylene naphthalate homopolymer or a crystallizable copolyester made up of residues of ethylene glycol, naphthalene dicarboxylic acid (NDC) and at least one member of the group (PA) consisting of terephthalic acid and isophthalic acid. The NDC groups make up about 5% or more of the sum of NDC and PA groups in the copolymer. The balloon is characterized by an ability to withstand a hoop stress of at least 35,000 psi without bursting.

17 Claims, 1 Drawing Sheet

U.S. PATENT DOCUMENTS

| | | | |
|---|---|---|---|
| 5,270,086 A | 12/1993 | Hamlin | 428/35.2 |
| 5,290,306 A | 3/1994 | Trotta et al. | 606/194 |
| 5,304,340 A | 4/1994 | Downey | 264/521 |
| 5,330,428 A | 7/1994 | Wang | 604/96 |
| 5,348,538 A | 9/1994 | Wang et al. | 604/96 |
| 5,403,340 A | 4/1995 | Wang et al. | 606/194 |
| 5,449,820 A | 9/1995 | Fukui et al. | 562/486 |
| 5,492,741 A | 2/1996 | Akao et al. | 428/35.2 |
| 5,500,181 A | 3/1996 | Wang et al. | 264/532 |
| 5,512,051 A | 4/1996 | Wang et al. | 604/96 |
| 5,554,120 A | 9/1996 | Chen et al. | 604/96 |
| 5,556,383 A | 9/1996 | Wang et al. | 604/96 |
| 5,587,125 A | 12/1996 | Roychowdhury | 264/515 |
| 5,871,468 A | 2/1999 | Kramer et al. | 604/96 |
| 5,879,369 A | 3/1999 | Ishida | 606/194 |
| 6,004,289 A | 12/1999 | Saab | 604/96 |
| 6,013,055 A | 1/2000 | Bampos et al. | 604/27 |
| 6,013,728 A | 1/2000 | Chen et al. | 525/92 |
| 6,242,063 B1 | 6/2001 | Ferrera et al. | 428/35.2 |
| 6,325,780 B1 | 12/2001 | Schaible et al. | 604/103.06 |
| 6,358,227 B1 | 3/2002 | Ferrera et al. | 604/103.06 |

OTHER PUBLICATIONS

Amoco product literature on PEN materials, pp. 3–5. Date unknown.

M. Cakmak et al., Processing Characteristics, Structure Development, and Proerties of Uni and Biaxially Stretched Poly(Ethylene 2,6 Naphthalene) PEN Films, *Polymer Engineering and Science*, vol. 30, No. 12, pp. 721–733, 1990.

Teijin Polyethylene Naphthalate Resin Technical Information. Predates Sep. 14, 1995.

D. Callander and E. Sisson, High Performance PEN & Naphthalate Based Packaging Resins, Shell Chemical Co., Apr. 1994.

D2857–70 Standard Method of Test for Dilute–Solution Viscosity of Polymers, 1970 Annual Book of ASTM Standards, Part 27, Plastics—General Method of Testing, Nomenclature, pp. 713–718.

Japanese Abstract, Appln No. 03174200, Filed Jul. 15, 1991.

Japanese Abstract, Appln No. 05088654, filed Apr. 15, 1993.

Fig.1
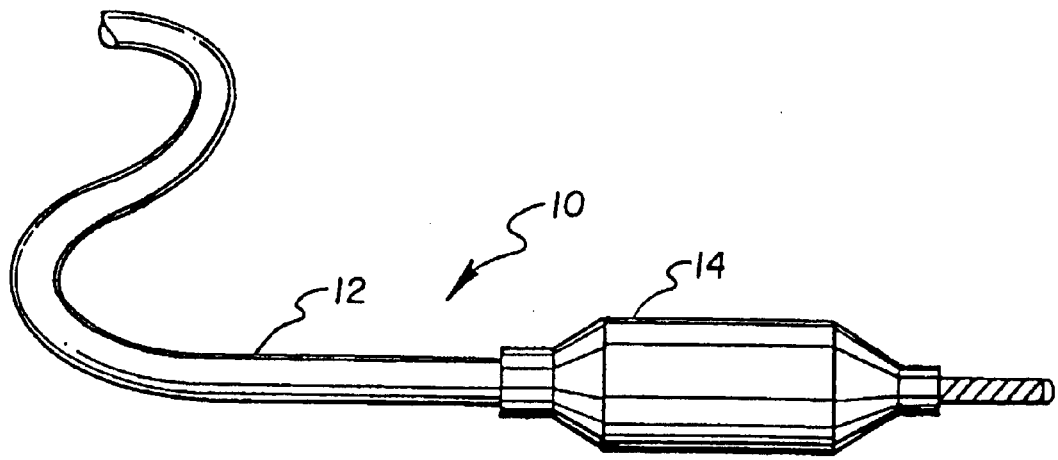
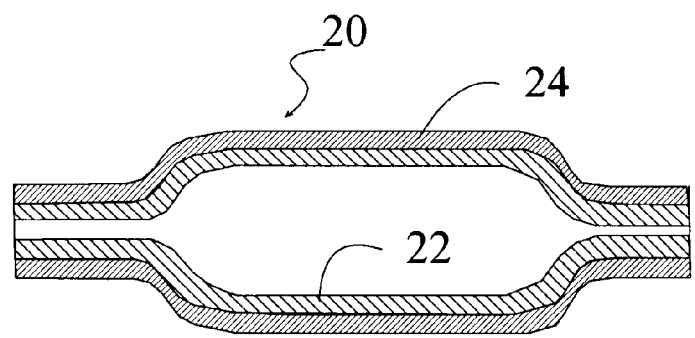
Fig. 2

DILATATION CATHETER BALLOON MADE FROM PEN BASED HOMOPOLYMER OR RANDOM COPOLYMER

CROSS REFERENCE TO RELATED APPLICATION

This application is a continuation of U.S. application Ser. No. 08/927,662, filed Sep. 10, 1997, now U.S. Pat. No. 6,358,227, issued Mar. 19, 2002, incorporated herein by reference in its entirety.

BACKGROUND OF THE INVENTION

The present PEN homopolymer and copolymer invention generally relates to a dilation catheter with an inflatable balloon which expands against the internal walls of a vessel to open or dilate a constriction, stenosis or occlusion of the vessel and, percutaneous transluminal angioplasty (PTA).

The PTA procedure places unique demands on the types of materials needed to fabricate a catheter fitted with an expandable balloon. The physical properties and characteristics of a desirable balloon may result in certain characteristics being balanced against others. For instance, very strong thermoplastic materials that are sufficiently strong enough to allow for minimum balloon wall thicknesses tend to be rigid, hard or stiff compared to more elastomeric materials that tend to be flexible, soft and deformable. Using stronger materials may give a minimum profile balloon but the stiffness of the material may be more likely to injure or traumatize the vascular system as the balloon is positioned to and then across a stenosis or occlusion.

In the art of catheter balloon manufacture, a variety of thermoplastic polymers have been used to prepare balloon structures. Polyethylene terephthalate (PET) of varying intrinsic viscosities have been widely commercialized.

In the past, PTA catheter balloons have been made from polymeric materials which gave balloons that may be broadly categorized into two groups: a) non-compliant balloons and b) compliant balloons.

Non-compliant balloons typically unfold to a nominal diameter and then stretch or expand only slightly beyond that diameter as the pressure is increased. See Levy, U.S. Pat. No. Re 32,983, Wang U.S. Pat. No. 5,195,969 and Wang U.S. Pat. No. 5,330,428. All three patents describe biaxially oriented polyethylene terephthalate (PET) balloons. In comparison compliant balloons typically inflate to a nominal diameter and then continue to stretch or expand as the inflation pressure is increased until the strength of the balloon material is exceeded and the balloon bursts. See Becker U.S. Pat. No. 4,154,244 and Wang, et al, U.S. Pat. No. 5,556,383.

In U.S. Pat. No. 5,270,086 it is proposed that a multilayer balloon could be made with an outer layer of a high tensile strength polymer and an inner bonding layer of a highly distensible polymer which had good melt bond and glue adhesion properties. Among the various materials proposed for the outer layer is polyethylene naphthalate. This reference, however, only exemplifies balloons in which the tensile layer is PET.

It has also been suggested that catheter balloons could be made of polyester/polyether block copolymers in which the polyester blocks were polyesters of naphthalene dicarboxylic acid (U.S. Pat. No. 5,556,383). To date, however, it has not been suggested that balloons made from polyethylene naphthalate could be formed in a manner to give properties significantly different from those of prior art balloons and it has not been demonstrated that such balloons could have substantially improved properties relative to commercial materials such as PET.

SUMMARY OF THE INVENTION

It has now been discovered that medical device balloons whose average strength is substantially higher than commercially standard PET balloons can readily be prepared from certain polyethylene naphthalate (PEN) homopolymers or copolymers. The high average strength of the PEN balloons is obtained even without exclusion of balloons having cosmetic defects, such as fish eyes or mottled surfaces.

The inventive catheter balloons have a structural layer of a polymer material of PEN homopolymer, or of a PEN copolymer which is a crystallizable copolyester made up of residues of ethylene glycol, of naphthalene dicarboxylic acid (NDC), and of a second dicarboxylic acid (PA) which is terephthalic acid or isophthalic acid, or a mixture thereof. The balloons are characterized by an ability to withstand a hoop stress of at least 35,000 psi without bursting, and can readily be designed to have a hoop stress of at least 50,000, even for larger diameter balloons having nominal diameters in the range of 6–30 mm.

The balloons of the invention may be either single layer balloons, or multilayer balloons. In one preferred embodiment the balloon comprises an inner layer of PEN homopolymer or copolymer and an outer layer of a polybutylene naphthalate polymer or copolymer.

BRIEF DESCRIPTION OF THE DRAWINGS

FIG. 1 is a perspective fragmentary view of a balloon catheter having a balloon thereon made in accordance with the invention.

FIG. 2 is a side sectional view of a balloon in accordance with one embodiment of the invention.

DETAILED DESCRIPTION OF PREFERRED EMBODIMENTS

Referring to FIG. 1 there is shown a catheter 10 comprising an elongated tube 12 with a balloon 14, made of a layer of PEN polymer in accordance with the invention hereof, mounted at the distal end thereof.

The PEN homopolymer used in the inventive balloons is a polyester, typically made by transesterification of dimethyl naphthalate and ethylene glycol. The PEN copolymers used in the inventive balloons are random polyester copolymers. In the copolymers the naphthalate groups (NDC) represent at least 5% of the diacid residues with the terephthalate and/or isophthalate units (PA) representing the balance. The PEN polymers are also highly crystallizable. As a practical matter, this latter feature limits the NDC/PA ratio to be either in the range of from about 5:95 to about 20:80 or in the range of from about 80:20 to 100:0. Preferably the NDC/PA ratio is in the range of from about 80:20 to 100:0. More preferably the minimum naphthalate content is about 90% of the diacid residue units, and even more preferably at least 95% of the diacid residues are naphthalate groups. The PEN homopolymers and PEN random copolymers preferably have an intrinsic viscosity less than 0.8 dl/g, measured under currently standard conditions for PET.

The PEN homopolymers and PEN copolymers used to make a catheter balloon of the present invention are prepared according to known procedures from ethylene glycol and naphthalene dicarboxylic acid or dimethyl naphthalenedicarboxylate, alone to produce homopolymer, or with dimethyl terephthalate and/or dimethyl isophthalate to produce copolymer. The naphthalene dicarboxylic acid monomer can be supplied by Amoco while some of the homopolymers and copolymers may be commercially available and are sold under the tradename Vituf® SLX by Shell Chemical, PEN Homopolymer 14991 by Eastman Chemical and various PEN homopolymer and copolymers sold by Teijin Ltd. of Tokyo, Japan under the designations TN8070; TN8060; TN8756T; and TN8880N and by Hoechst Trevira GmbH & Co. KG, under the trademark Polyclear, including Polyclear N10, Polyclear N90 and Polyclear N100.

The balloons of the invention are particularly suited for use on dilatation catheters used for percutaneous transluminal angioplasty and other minimally invasive procedures. The balloon diameter maybe from about 1.5 to about 30 mm, depending on the application to which it is put. The balloons are substantially non-compliant, typically providing a radial expansion of less than 3% when inflation pressure is increased from about 4 atm to about 10 atm, even for relatively large balloons of 6–30 mm. The balloons of the invention are engineered to provide a maximum hoop stress at burst, of about 35,000 psi or more, suitably above 50,000, and typically in the range of 55,000–65,000 psi.

The PEN homopolymers and PEN/PET copolymer catheter balloons of this invention are suitably formed to provide a double wall thickness, measured on the uninflated collapsed balloon, of about 0.0002"–0.0020".

In one preferred embodiment of the invention, balloon formation is begun by extruding a tube from a melt of the polymer material. Some initial orientation of the PEN homopolymers and PEN/PET copolymers is accomplished as the material is drawn down during the extrusion process. This process is typically known as machine orientation and is in the direction of the extrusion operation. It is desirable that the machine orientation be controlled to minimize orientation during extrusion.

Following extrusion, the extruded tube is desirably conditioned at 20–30° C. at a controlled humidity in the range of 10–25% for a period of at least 24 hours. This conditioning provides a constant low moisture level in the tube which prevents hydrolysis and helps to optimize the orientation of the polymer in the subsequent blowing steps.

Principle orientation in the machine and transverse directions may be achieved by heating the tubing to temperatures of 135°–165° C. and physically stretching the extruded homopolymer or random copolymer tube in the axial and radial direction during balloon formation using a free blowing technique. In this step a pressurized gas is applied to the inside of the tubing. The tubing is expanded freely to a specified diameter between cone forms which define the balloon length and cone wall configuration. A similar blowing step is described in U.S. Pat. No. 4,963,313. The blowing pressure and stretching ratio in the machine and transverse directions have a controlling effect on final balloon wall thickness. The axial stretch ratio in this step is suitably from about 2x to about 5x. The radial stretch is suitably from about 3x to about 12x. The tubing diameter to which the balloon is blown in this step is selected so that, after quenching, the inflated but unstressed balloon will have a diameter in the range of about 50–95% of the final diameter desired for the balloon. Suitable inflation pressure for this step are in the range of about 100–180 psi, depending on balloon size. Once the balloon reaches the specified diameter it is quenched to room temperature and depressurized.

The balloon may be finished in a second, mold blow/crystallization, step. In this step the partially formed balloon of the previous step is placed in a mold sized to the final diameter and shape desired for the balloon. The mold is closed and the balloon pressurized to prevent shrinkage, suitably at a pressure of about 5–50 psi. The mold is heated to bring the balloon material to a temperature of about 10–60° C. above the Tg of the balloon material, with pressurization of the balloon sufficient to expand it to the final desired diameter (typically 170–250 psi). This temperature and pressure is held for a brief time, suitably about 5–60 seconds, after which the mold is rapidly quenched to ambient temperature and the balloon removed from the mold.

The final balloons may have a number of visible cosmetic defects, such as fish eyes or mottled surfaces. Surprisingly such defects do not appear to reduce balloon strength, indicating a remarkable toughness in the finished balloon.

In another embodiment the balloon is a plural layer laminate including a layer of the PEN polymer as described herein and an outer layer of a softer more elastomeric polymer to provide improved puncture resistance and to provide a softer less scratchy surface texture to reduce vessel trauma in use. Various techniques are known for producing such multilayer structures, including coextrusion as described in U.S. Pat. No. 5,195,969 (J. Wang, et al.), U.S. Pat. No. 5,290,306 (Trotta et al) and U.S. Pat. No. 5,270,086 (Hamlin), and tube-in-tube techniques as described in copending U.S. application Ser. No. 08/611,664, filed Mar. 6, 1996, U.S. Pat. No. 5,512,051 (J. Wang, et al) and in WO 96/04951 (Schneider Inc.). The higher extrusion, blowing and crystallization temperatures required for the PEN polymers used in the invention, however, can make identification of satisfactory outer layer polymers difficult. This is particularly so for coextrusions since the temperature at which the extruder must be heated to melt and extrude the PEN polymer melt temperature can exceed the temperature at which many softer compliant thermoplastic polymers begin to thermally degrade. A particularly preferred multilayer laminate structure of the invention is formed from a coextruded tube having an inner layer of a PEN polymer as described above and an outer layer of a polybutylene naphthalate/phthalate copolyester. Such copolyesters have good thermal stability and process well at the melt and the subsequent processing temperatures employed for the PEN polymer. An example of a suitable polybutylene naphthalate/phthalate copolyester is Nouvelan®, sold by Teijin, Ltd., Japan, a naphthalate/terephthalate copolyester.

Referring to FIG. 2 there is shown a catheter balloon 20 comprising an inner layer 22 of a PEN homopolymer or copolymer as described herein, and an outer layer 24 of a polybutylene naphthalate/phthalate copolyester.

Those skilled in the art will recognize that other techniques known for preparing medical device balloons of other thermoplastic polymer materials can be readily modified in accordance with the teachings and observations provided herein, and without undue experimentation, to produce balloons according to the present invention.

In addition to structural polymer layers, the balloon may be provided with a nonstructural coating layer, for instance a coating of a lubricious polymer or of a antithrombotic material, to improve surface properties of the balloon.

The invention is illustrated by the following non-limiting examples.

EXAMPLE 1

Tubing of dimension 0.0257 inch ID and 0.056 inch OD was extruded from Teijin TN8880N, a linear polyester copolymer ethylene glycol, the diacid residue of which contains 8% naphthalate and 92% terephthalate units. The tubing was subjected to a two step balloon formation process (free-blow followed by mold-blow/crystallization), as described above, using inflation pressure and times selected to provide a total circumferential growth factor of about 9.1 and an axial growth factor of about 3.8 to yield final balloons of 6 mm diameter with a single wall thickness of 0.0007 inch. Many balloons displayed some fisheye or mottled surface defects. No balloons were excluded for cosmetic defect. The balloons so prepared had an average hoop stress at burst of approximately 55,700 psi.

EXAMPLE 2

Tubing of dimension 0.022 inch ID and 0.054 inch OD was extruded from a commercial PEN homopolymer having an intrinsic viscosity of 0.7. The tubing was formed into 5 mm balloons in a manner similar to Example 1 using a circumferential growth factor of about 8.8 and an axial growth factor of about 3.7. The final balloons had an average single wall thickness of 0.0009 inch. Many balloons displayed some fisheye or mottled surface defects. No balloons were excluded for cosmetic defect. The balloons so prepared had an average hoop stress at burst of approximately 56,100 psi.

EXAMPLE 3

Tubing of dimension 0.028 ID and 0.056 OD was extruded from Teijin TN8880N. The tubing was subjected to a two step balloon formation process (free-blow followed by mold-blow/crystallization), as described above, to yield final balloons of 6 mm diameter with a double wall thickness of 0.0011–0.0013 inches.

In the second step (mold-blow/crystallization), groups of 15 balloons each were made using mold temperatures increasing at 5° C. increments from 140° C. to 175° C. Many balloons displayed some fisheye or mottled surface defects. No balloons were excluded for cosmetic defect.

At least 14 balloons were burst tested from each group. Balloons mounted on test catheter shafts were inflated at 1 atm intervals until burst. Compliance over the range 74–147 psi inflation pressure was determined from diameter measurements taken at successive pressure intervals. Average hoop stresses at burst for the various balloon groups ranged from 56,000–60,000 psi. Average compliance for the various balloon groups ranged between 1.4 and 2.0%.

With only one possible exception, it did not appear that balloons having cosmetic defects failed at a significantly lower pressure than others in its group.

What is claimed is:

1. A medical catheter having thereon a balloon, the balloon comprising a structural layer of a PEN polymer material, the PEN polymer material being
    a) a polyethylene naphthalate homopolymer or
    b) a crystallizable copolyester comprising residues of
        i) ethylene glycol,
        ii) naphthalene dicarboxylic acid and
        iii) at least one PA residue, said PA residue being a member of the group consisting of residues of terephthalic acid and isophthalic acid, the naphthalene dicarboxylic acid residues comprising about 5% or more of the sum of naphthalene dicarboxylic acid residues and PA residues in the copolyester, and,
the balloon characterized by an ability to withstand a hoop stress of at least 50,000 psi without bursting.

2. A catheter as in claim 1 wherein the balloon has a double wall thickness of from 0.0002" to about 0.002".

3. A catheter as in claim 1 wherein the PEN polymer material is said polyethylene naphthalate homopolymer.

4. A catheter as in claim 1 wherein the balloon has a radial expansion of about 3% or less when inflation pressure is increased from 4 atm to burst.

5. A catheter as in claim 1 wherein the balloon has a diameter of about 6 mm or more and an average burst pressure of about 17 atm or more.

6. A catheter as in claim 1 wherein the balloon comprises at least two structural layers, one being said PEN polymer layer and one being a layer of a second thermoplastic polymer material.

7. A catheter as in claim 6 wherein the balloon has inner and outer sides and the second thermoplastic polymer material is a coextruded layer on the outer side thereof.

8. A catheter as in claim 1 wherein the balloon has a single structural polymer layer.

9. A catheter as in claim 1 wherein said hoop stress is within the range of 55,000 to 65,000 psi.

10. A medical catheter having thereon a balloon comprising a structural layer of a crystallizable copolyester comprising residues of
    i) ethylene glycol,
    ii) naphthalene dicarboxylic acid and
    iii) at least one PA residue, said PA residue being a member of the group consisting of residues of terephthalic acid and isophthalic acid,
the naphthalene dicarboxylic acid residues constituting at least 80% of the sum of naphthalene dicarboxylic acid residues and PA residues.

11. A catheter as in claim 10 wherein said naphthalene dicarboxylic acid residues constitute at least 95% of said sum of naphthalene dicarboxylic acid residues and PA residues.

12. A catheter as in claim 10 wherein said PA residues are terephthalic acid residues.

13. A catheter as in claim 10 wherein the balloon has a single structural polymer layer.

14. A catheter as in claim 13 wherein said PA residues are terephthalic acid residues.

15. A catheter as in claim 13 wherein the balloon has a single structural polymer layer.

16. A catheter as in claim 13 wherein the balloon further comprises a layer of a second polymer, said second polymer being a polybutylene naphthalate homopolymer or a butylene naphthalate copolymer.

17. A medical catheter having a balloon thereon, the balloon comprising at least two structural layers,
    one layer being a PEN polymer layer, the PEN polymer material being
        a) a polyethylene naphthalate homopolymer or
        b) a crystallizable copolyester comprising residues of
            i) ethylene glycol,
            ii) naphthalene dicarboxylic acid and
            iii) at least one PA residue, said PA residue being a member of the group consisting of residues of terephthalic acid and isophthalic acid, the naphthalene dicarboxylic acid residues at least 80% of the sum of naphthalene dicarboxylic acid residues and PA residues in the copolyester, and
    one layer being a polybutylene naphthalate homopolymer or a butylene naphthalate copolymer.

* * * * *